(12) United States Patent  
Sloop et al.

(10) Patent No.: US 10,613,064 B2  
(45) Date of Patent: Apr. 7, 2020

(54) NETWORK FOR MEASURING GREENHOUSE GASES IN THE ATMOSPHERE

(71) Applicants: Earth Networks, Inc., Germantown, MD (US); The Regents of the University of California, Oakland, CA (US)

(72) Inventors: Christopher Dale Sloop, Mount Airy, MD (US); Elena Novakovskaia, Chappaqua, NY (US); Robert S. Marshall, Ijamsville, MD (US); Ray F. Weiss, La Jolla, CA (US); Ralph Keeling, San Diego, CA (US); Lisa Welp-Smith, San Diego, CA (US)

(73) Assignees: Earth Networks, Inc., Germantown, MD (US); The Regents of the University of California, Oakland, CA (US)

( * ) Notice: Subject to any disclaimer, the term of this patent is extended or adjusted under 35 U.S.C. 154(b) by 151 days.

(21) Appl. No.: 15/267,110

(22) Filed: Sep. 15, 2016

(65) Prior Publication Data

US 2017/0003260 A1  Jan. 5, 2017

Related U.S. Application Data

(63) Continuation of application No. 13/737,508, filed on Jan. 9, 2013, now Pat. No. 9,448,214.

(51) Int. Cl.  
*G01N 33/00*   (2006.01)

(52) U.S. Cl.  
CPC ..... *G01N 33/0006* (2013.01); *G01N 33/0004* (2013.01)

(58) Field of Classification Search  
CPC .................... G01N 33/00006; G01N 33/0004  
USPC .......................................................... 73/1.06  
See application file for complete search history.

(56) References Cited

U.S. PATENT DOCUMENTS 4,635,735 A * 1/1987 Crownover ........... E21B 21/067  
175/42  
7,154,595 B2  12/2006 Paldus et al.  
(Continued)

FOREIGN PATENT DOCUMENTS

CN  101482501 B  7/2009  
CN  102338750 A  2/2012  
(Continued)

OTHER PUBLICATIONS

Aoki, T., "Path-radiance correction by polarization observation of Sun glint glitter for remote measurements of tropospheric greenhouse gases," Applied Optics, vol. 41, No. 24, published Aug. 20, 2002, pp. 4945-4957.

(Continued)

*Primary Examiner* — John Fitzgerald  
*Assistant Examiner* — Rodney T Frank  
(74) *Attorney, Agent, or Firm* — Proskauer Rose LLP

(57) ABSTRACT

Methods and apparatuses, including computer program products, are described for measuring greenhouse gas. A calibration device receives a first sample of atmospheric gas from a first port exposed to the earth's atmosphere. The calibration device receives a second sample of atmospheric gas from a second port exposed to the earth's atmosphere. The calibration device routes the first sample and the second sample to a measurement device for greenhouse gas analysis. The measurement device determines a characteristic of a greenhouse gas present in at least one of the first sample and the second sample. The measurement device transmits data associated with the determined characteristic of the greenhouse gas to a computing device for determining sinks and sources of the gas.

9 Claims, 10 Drawing Sheets

(56) References Cited

U.S. PATENT DOCUMENTS

| | | |
|---|---|---|
| 2006/0262311 A1 | 11/2006 | Muta et al. |
| 2007/0233502 A1 | 10/2007 | Richards et al. |
| 2008/0151248 A1 | 6/2008 | Cole et al. |
| 2010/0042453 A1 | 2/2010 | Scaramellino et al. |
| 2010/0198736 A1 | 8/2010 | Marino |
| 2011/0040493 A1 | 2/2011 | Choi et al. |
| 2011/0055220 A1 | 3/2011 | Tyburski |
| 2011/0072814 A1 | 3/2011 | Tice |
| 2013/0179078 A1 | 7/2013 | Griffon |

FOREIGN PATENT DOCUMENTS

| | | |
|---|---|---|
| JP | 2006133200 A | 5/2006 |
| WO | 1999042814 A1 | 8/1999 |

OTHER PUBLICATIONS

Blaine, T.W., "Continuous Measurements of Atmospheric Ar/N2 as a Tracer of Air-Sea Heat Flux: Models, Methods, and Data," University of California, San Diego, dated 2005, 225 pages.

Crosson, E.R., "A cavity ring-down analyzer for measuring atmospheric levels of methane, carbon dioxide, and water vapor," Applied Physics B, vol. 92, Issue 3, Sep. 2008, pp. 403-408.

Herbst, M., "Climate and site management as driving factors for the atmospheric greenhouse gas exchange of a restored wetland," Biogeosciences 10, pp. 39-52, published Jan. 7, 2013.

LI-7500 CO2/H2O Analyze Instruction Manual, LI-COR Environmental Division, publication No. 984-06360, dated 2003, 157 pages.

Marty, C.A., "Surface Radiation, Cloud Forcing and Greenhouse Effect in the Alps," Swiss Federal Institut of Technology Zurich, Diss. ETH No. 13609, dated Mar. 2000, 140 pages.

Picarro Automated Multi-Point Greenhouse Gas Measurement System, available at https://www.picarro.com/assets/docs/Picarro_AN016_Tall_Tower_GHG_Measurements.pdf, 2008, 4 pages.

International Search Report and Written Opinion of the International Searching Authority for PCT/US14/10342 dated Apr. 21, 2014, 15 pages.

\* cited by examiner

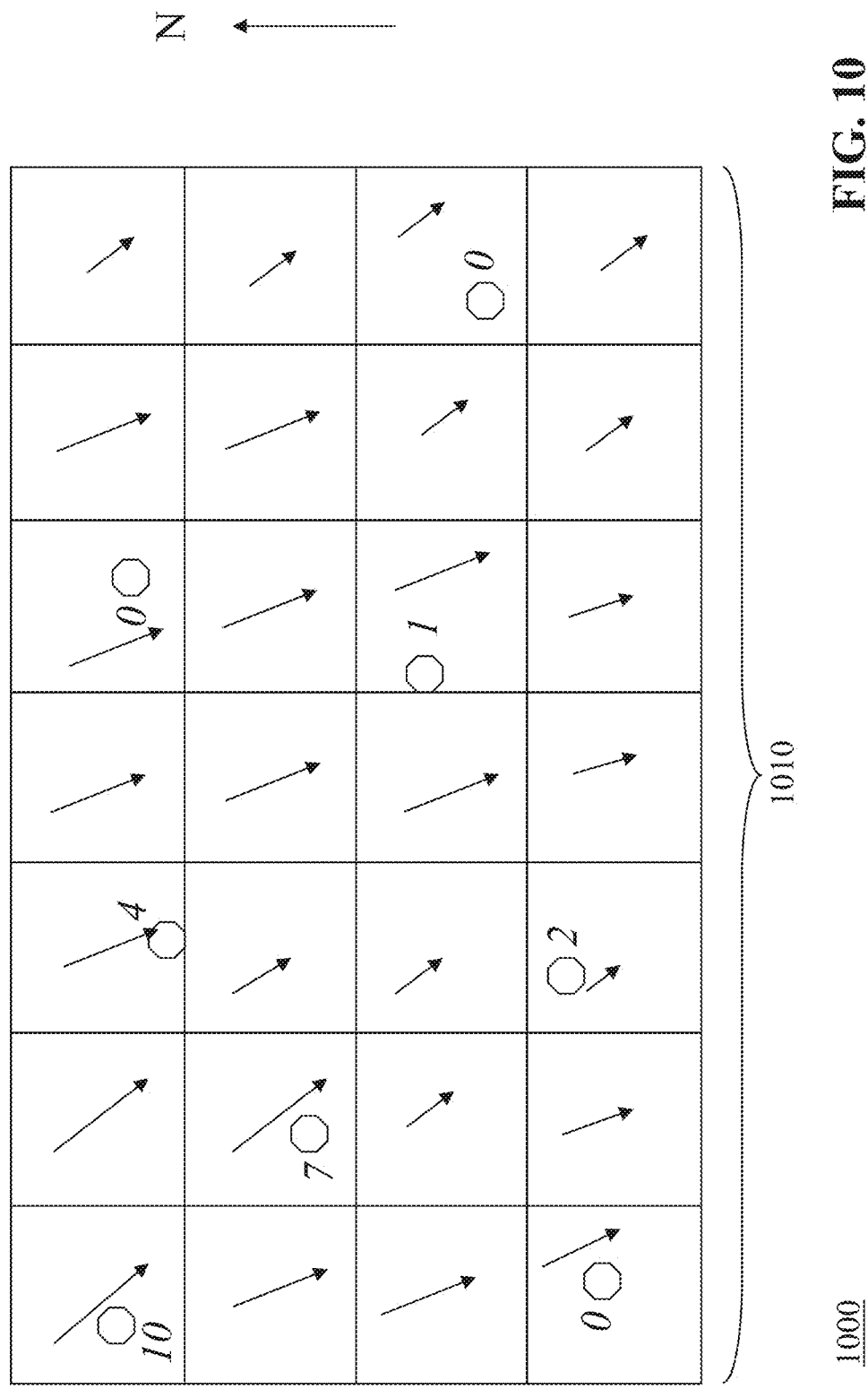

NETWORK FOR MEASURING GREENHOUSE GASES IN THE ATMOSPHERE

RELATED APPLICATIONS

This application is a continuation of U.S. patent application Ser. No. 13/737,508, filed on Jan. 9, 2013, the entirety of which is incorporated herein by reference.

TECHNICAL FIELD

The subject matter of this application relates generally to methods and apparatuses, including computer program products, for measuring greenhouse gases in the atmosphere and determining sinks and sources of these gases.

BACKGROUND

The release of greenhouse gas into the atmosphere has significant environmental and economic impact on a worldwide scale. Local, state and federal governments are under increasing pressure to monitor and regulate greenhouse gas emissions to prevent further damage to the earth's climate and environment. One challenge has been to accurately measure greenhouse gases in the atmosphere over a distributed geographical area to determine the location of potential sources of greenhouse gases.

SUMMARY

In general overview, the techniques described herein are related to the measurement of greenhouse gases in the atmosphere, the calibration of devices to perform the measurement, and the determination of sinks and sources of greenhouse gases. The techniques provide for real-time, continuous measurement of atmospheric greenhouse gases across a distributed geographic area. The techniques also provide for improved calibration of in situ greenhouse gas measurement devices by automating and controlling the testing and operation of the devices. The techniques also provide for collection, modeling and analysis of the greenhouse gas measurement data to accurately determine the location of potential greenhouse gas sinks and sources.

The invention, in one aspect, features a method for measuring greenhouse gas. The method includes receiving, at a calibration device, a first sample of atmospheric gas from a first port exposed to the earth's atmosphere and receiving, at the calibration device, a second sample of atmospheric gas from a second port exposed to the earth's atmosphere. The method includes routing, by the calibration device, the first sample and the second sample to a measurement device for greenhouse gas analysis. The method includes determining, by the measurement device, a characteristic of a greenhouse gas present in at least one of the first sample and the second sample; and transmitting, by the measurement device, data associated with the determined characteristic of the greenhouse gas to a computing device.

The invention, in another aspect, features a method for calibrating a greenhouse gas measurement device. The method includes receiving, at a calibration device, a first greenhouse gas amount from a pump coupled to the calibration device. The method includes passing, via the calibration device, the first greenhouse gas amount to the measurement device. The method includes determining, by the measurement device, a characteristic of a greenhouse gas present in the first greenhouse gas amount and transmitting, by the measurement device, the characteristic to a computing device. The method includes calibrating, by the computing device, the characteristic by applying a correction to the characteristic.

The invention, in another aspect, features a system for measuring greenhouse gas in the atmosphere. The system includes a calibration device configured to receive a first sample of atmospheric gas from a first port exposed to the earth's atmosphere, and receive a second sample of atmospheric gas from a second port exposed to the earth's atmosphere. The calibration device is configured to route the first sample and the second sample to a measurement device for greenhouse gas analysis. The system includes the measurement device, which is configured to determine a characteristic of a greenhouse gas present in at least one of the first sample and the second sample, and transmit data associated with the determined characteristic of the greenhouse gas to a computing device.

The invention, in another aspect, features a device for calibrating a greenhouse gas measurement device. The device includes one or more inlets for receiving samples of atmospheric gas from one or more ports exposed to the earth's atmosphere, and one or more pumps for regulating a flow of the atmospheric gas received via the inlets. The device includes one or more calibration tanks and a sampling module. The sampling module includes a valve coupled to the one or more pumps and the one or more calibration tanks, a pressure and temperature controller, and a dryer. The sampling module is configured to sample gas from one or more of the pumps and calibration tanks using the valve, regulate pressure and temperature of the sampled gas using the pressure and temperature controller, remove water vapor from the sampled gas using the dryer, and convey the gas from the dryer to a measurement device configured to determine a characteristic of a greenhouse gas present in the sampled gas.

The invention, in another aspect, features a method for measuring greenhouse gas. The method includes receiving, at a server computing device from two or more in situ measurement devices, a value representing the amount of greenhouse gas contained in a sample of atmospheric gas collected at the location of the two or more in situ measurement devices. The method includes receiving, at the server computing device from two or more weather observation instruments located at or near the location of the two or more in situ measurement devices, atmospheric conditions data. The method includes comparing, by the central computing device, the greenhouse gas amount values received from the two or more in situ measurement devices to determine similarities and differences between the respective greenhouse gas amount values. The method includes comparing, by the server computing device, the atmospheric conditions data received from the two or more weather observation instruments to determine similarities and differences between the respective atmospheric conditions data.

In some embodiments, any of the above aspects can include one or more of the following features. In some embodiments, the first port is located at least 80 meters off the ground. In some embodiments, the second port is located at the same position as the first port. In some embodiments, the second port is separated from the first port by at least 20 meters.

In some embodiments, the routing step includes determining the pressure and temperature of at least one of the first sample and the second sample, transmitting the determined pressure and temperature to the computing device, applying a drying agent to at least one of the first sample and the second sample, and passing at least one of the first sample and the second sample to the measurement device. In some embodiments, the drying agent absorbs water vapor from the at least one of the first sample and the second sample.

In some embodiments, the measurement device uses cavity ring-down laser spectroscopy to determine the characteristic of the greenhouse gas in the at least one of the first sample and the second sample. In some embodiments, the data associated with the determined characteristic of greenhouse gas includes a numeric value corresponding to an amount of greenhouse gas, atmospheric conditions data associated with the location of the first port and second port, and timestamp data.

In some embodiments, the measurement device receives a schedule, and the measurement device receives at least one of the first sample and the second sample based on the schedule. In some embodiments, a display device coupled to the computing device displays the data associated with the determined characteristic of greenhouse gas.

In some embodiments, the calibration device receives a first greenhouse gas amount from a pump coupled to the calibration device, passes the first greenhouse gas amount to the measurement device, and calibrates a measuring instrument in the measurement device used to measure greenhouse gas based on the first greenhouse gas amount. In some embodiments, the calibration device is configured to receive a first greenhouse gas amount from a pump coupled to the calibration device, pass the first greenhouse gas amount to the measurement device, and calibrate a measuring instrument in the measurement device used to measure greenhouse gas based on the first greenhouse gas amount.

In some embodiments, the sampling module is configured to measure the pressure of the sampled gas, and transmit the measured pressure value to the measurement device. In some embodiments, a sampling controller coupled to the valve is configured to instruct the valve to sample gas from one of the one or more pumps or one of the one or more calibration tanks. In some embodiments, the sampling controller instructs the valve to sample gas from the one or more pumps and the one or more calibration tanks in a predetermined sequence.

In some embodiments, the inlets are coupled to the ports via a tube. In some embodiments, the atmospheric gas received by the one or more inlets is air. In some embodiments, at least one of the one or more calibration tanks contains a gas used for zeroing the calibration device. In some embodiments, the valve is further coupled to an auxiliary intake configured to access an additional gas source. In some embodiments, the sampling device is configured to receive quality control data from the calibration device, and adjust the sampling of gas based on the quality control data.

In some embodiments, the determining step is based on inverse modeling of the aggregated data. In some embodiments, the atmospheric conditions data includes wind speed and wind direction, the aggregating step further comprising generating a geographical grid representing a probabilistic amount of the greenhouse gas in the atmosphere and the movement of the greenhouse gas based on the atmospheric conditions data. In some embodiments, the server computing device receives the greenhouse gas amount values and the atmospheric conditions data in real time.

In some embodiments, the aggregating step includes determining a potential source of the greenhouse gas in the area of interest exposed to the in situ measurement devices, where the determining a potential source of the greenhouse gas is based on pre-stored information. In some embodiments, the determining step estimates the location of greenhouse gas sinks and greenhouse gas sources. In some embodiments, the estimated location of sinks and sources includes an uncertainty range. In some embodiments, the determining step is performed substantially in real time.

In some embodiments, the server computing device aggregates the greenhouse gas amount values and the atmospheric conditions data according to the location of the in situ measurement devices and the weather observation instruments, and determines the source of the greenhouse gas based on the aggregation step and the comparison steps.

Other aspects and advantages of the invention will become apparent from the following detailed description, taken in conjunction with the accompanying drawings, illustrating the principles of the invention by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 10 is a diagram of computing impacts on the surface elements on the measurements of greenhouse gases by the network that is a step in the inversion report generated by the system for measuring greenhouse gas in the atmosphere.

DETAILED DESCRIPTION

Figure 1:
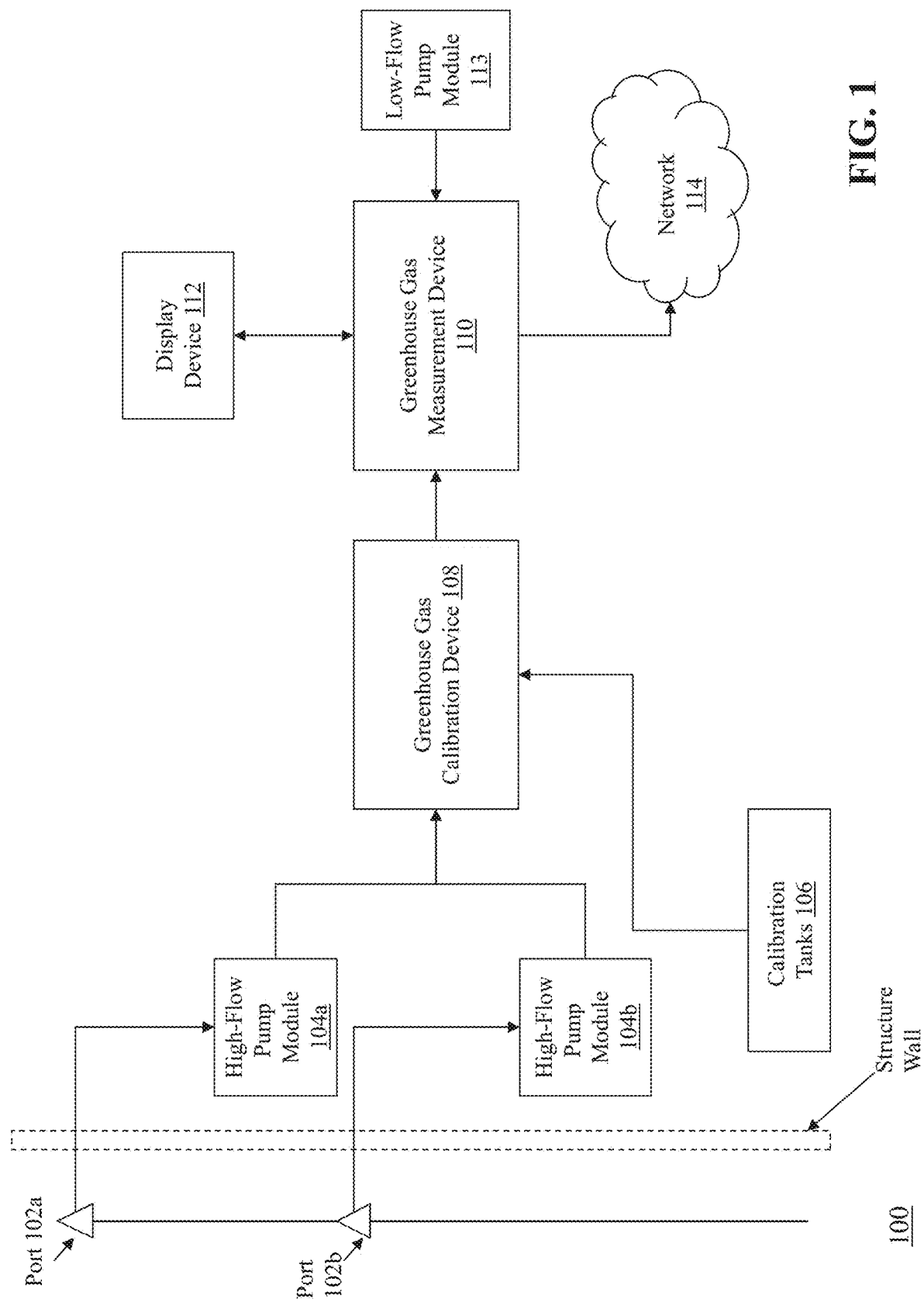
FIG. 1 is a block diagram of a system for measuring greenhouse gas in the atmosphere.

FIG. 1 is a block diagram of a system 100 for measuring greenhouse gas in the atmosphere. The system 100 includes ports 102a and 102b, high-flow pump modules 104a and 104b, calibration tanks 106, greenhouse gas calibration device 108, greenhouse gas measurement device 110, display device 112, and low-flow pump module 113. The system 100 is connected to a communications network 114.

The ports 102a and 102b are positioned in an external location, for example on a tower outside of a building or other structure that houses the remaining components of the system 100. The ports 102a and 102b sample atmospheric gas and route the sampled gas to pump modules (e.g., 104a and 104b). It should be appreciated that the amount of sampled gas can vary based on the devices used to implement the system 100. For example, in some embodiments, the measurement device 110 samples a pre-defined volume of gas according to the size of a cavity within the device 110. Based on the particular measurement device used in the system 100, the amount of sampled gas can be greater or less than another measurement device. For example, some systems may require only a small amount of sampled gas while other systems may require a larger amount.

Also, the amount of sampled gas can depend upon the length of time that the measurement device 110 samples the gas. For example, the sampling interval in some measurement devices 110 can be longer than the sampling interval in other measurement devices. It should be noted that the sampling techniques described herein are not intended to modify the composition of the environment from which the gas is sampled. Instead, the sampling techniques simply allow for measurement of the sampled gas.

The ports 102a and 102b are coupled to the pump modules 104a and 104b via a conduit (e.g., pipes, tubes) that allows the sampled gas to reach the pump modules 104a and 104b. The conduit is preferably composed of a material that withstands corrosion and other deleterious effects caused by exposure to the atmosphere, and can maintain its structural integrity without additional support when spanning large distances. In some embodiments, the conduit can be ⅜-inch Synflex® 1300 flexible tubing.

In some embodiments, port 102a is located on the tower at a height of at least eighty meters and port 102b is located on the tower at a height at least twenty meters below port 102a. An advantage provided by locating port 102a at a height of at least eighty meters is the ability to sample greenhouse gas that has been emitted into the atmosphere at further distances (e.g., from gas sources located far away). For example, if port 102a is located too close to the ground, the sampled gas may contain greenhouse gas from certain ground-level sources (e.g., vehicles) that can affect the measurement and analysis of the samples. The height difference between port 102a and 102b allows the system 100 to measure greenhouse gas at different levels of the atmosphere and also determine the amount of greenhouse gas mixing between the levels of the atmosphere.

It should be appreciated that the system 100 is not limited to having two ports 102a and 102b as shown in FIG. 1, but any number of ports can be used and the location of the ports can be adjusted without departing from the spirit and scope of the invention. In some embodiments, the system 100 has two ports located at the same height (e.g., eighty meters) for quality control and/or redundancy purposes. Also, in some embodiments, the tower includes other measuring and monitoring equipment, such as a weather observation instrument (not shown). The data collected by the weather observation instrument (e.g., wind speed, ambient pressure and temperature, humidity) can be provided to and recorded by the system 100 for use as part of the greenhouse gas analysis.

Figure 2:
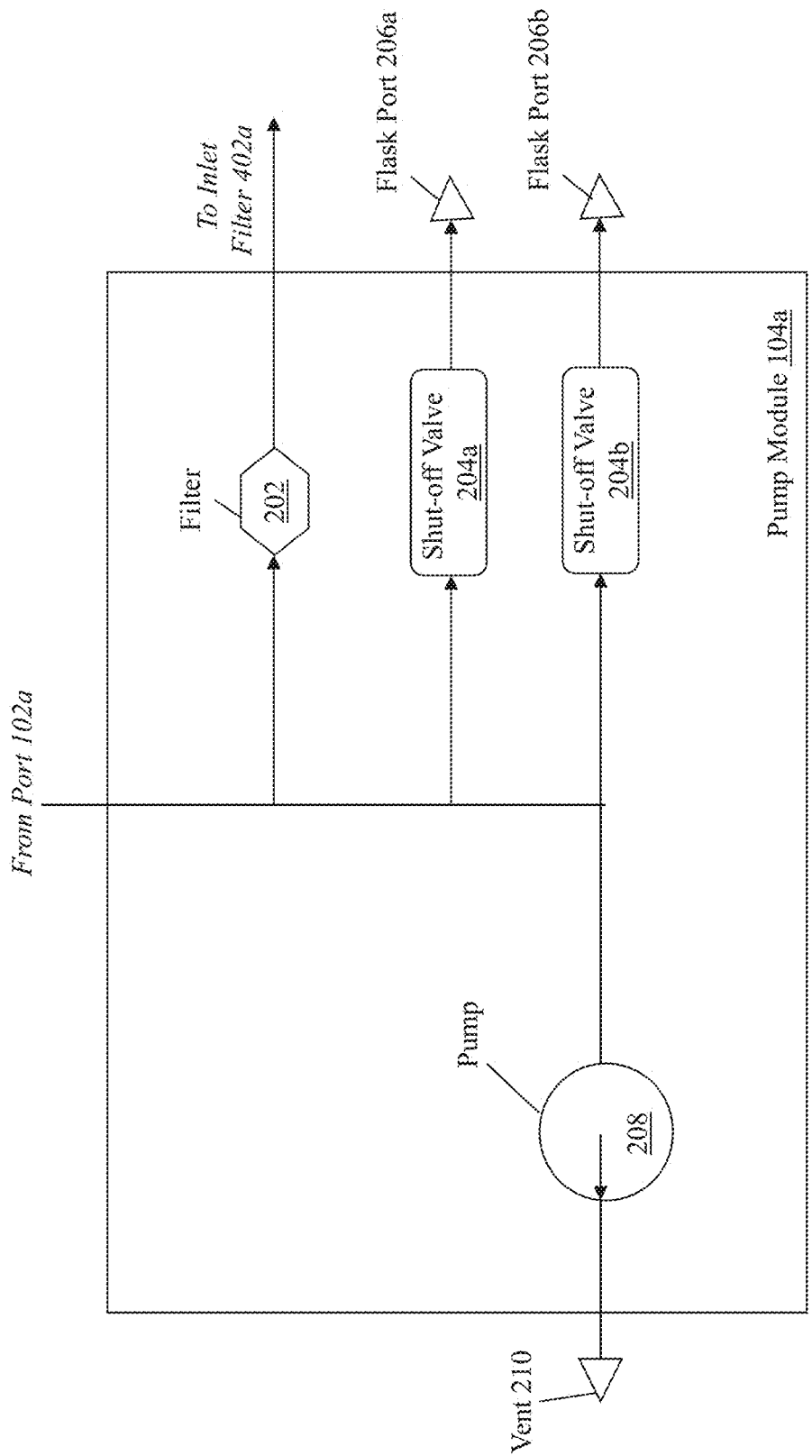
FIG. 2 is a detailed block diagram of a pump module of the system for measuring greenhouse gas in the atmosphere.

The system 100 also includes high-flow pump modules 104a and 104b. FIG. 2 is a detailed block diagram 200 of a high-flow pump module (e.g., module 104a) of the system 100. The high-flow pump module 104a receives sampled atmospheric gas from ports 102a. The pump module 104a includes a filter 202 to remove any particulates or other unwanted substances from the sampled gas before the gas is transmitted to the greenhouse gas calibration module 108. The high-flow pump module 104a also includes shut-off valves 204a and 204b, each connected to a flask port 206a and 206b, respectively. The shut-off valves 204a and 204b, and flask ports 206a and 206b, provide auxiliary access to the high-flow pump module 104a for purposes of maintenance and testing. For example, a flask port 206a can be used to capture a portion of the sampled gas for external analysis or other comparative analysis.

The high-flow pump module 104a also includes a linear oscillating pump 208. The pump 208 regulates and controls the flow rate of the sampled gas sampled from port 102a. The pump module 104a also includes a vent 210 to release a portion of the sampled gas if desired; the vent 210 operates to regulate the pressure of the sampled gas within the pump module 104a. In some embodiments, the components 202, 204a-204b, 206a-206b, 208 and 210 of the pump module 104a are coupled together using a ¼-inch Synflex® 1300 flexible tubing.

Figure 3:
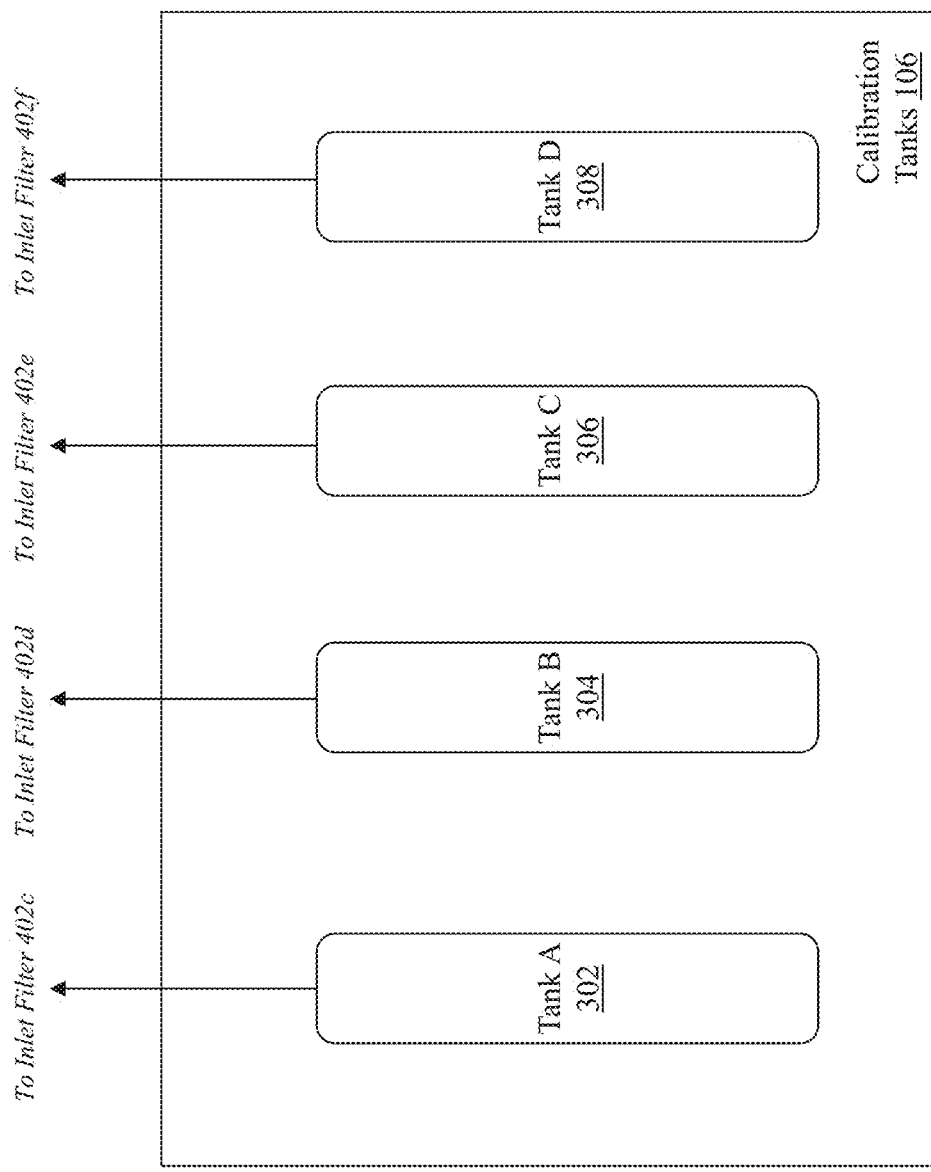
FIG. 3 is a detailed block diagram of a plurality of calibration tanks of the system for measuring greenhouse gas in the atmosphere.

As shown in FIG. 1, the system 100 also includes a plurality of calibration tanks 106 coupled to the greenhouse gas calibration device 108. FIG. 3 is a detailed block diagram 300 of the plurality of calibration tanks 106 of the system 100. The calibration tanks 302, 304, 306, 308 contain quantities of gas used by the system 100 to calibrate the components that measure the amount of greenhouse gas in the samples obtained from the atmosphere. For example, in some embodiments, Tank A 302 contains carbon dioxide ($CO_2$), Tank B 304 contains methane ($CH_4$), Tank C 306 contains carbon monoxide (CO), and Tank D 308 contains a zero gas (e.g., Nitrogen) having none of the greenhouse gases present for which the system 100 is currently testing. By using the calibration tanks, the system 100 can perform calibration analysis associated with the measurement device 110.

For example, to ensure that the measuring instrument in the measurement device 110 is providing accurate readings, the calibration device 108 can collect a quantity of gas from one or more of the calibration tanks 302, 304, 306, 308 and transmit the collected gas to the measurement device 110. The collected gas should contain a known quantity of the greenhouse gas, so the reading provided by the measurement device 110 for the collected gas can be compared against the expected value to determine whether the measurement device 110 needs adjustment or maintenance. The calibration device 108 can also use the calibration tanks to reset the measurement device 110 before performing additional measurements of sampled gas from the atmosphere. In some embodiments, the calibration device 108 receives an instruction from a local processor or computing device to reset the measurement device 110.

The calibration tanks 302, 304, 306, 308 also include pressure gauges, regulators and relief valves to control and monitor the flow rate of the gas. The calibration tanks 302, 304, 306, 308 are each coupled to the greenhouse gas calibration device 108 via a separate conduit. In some embodiments, the conduits between the calibration tanks and the greenhouse gas calibration device 108 are made up of 1/16-inch stainless steel tubing.

Figure 4:
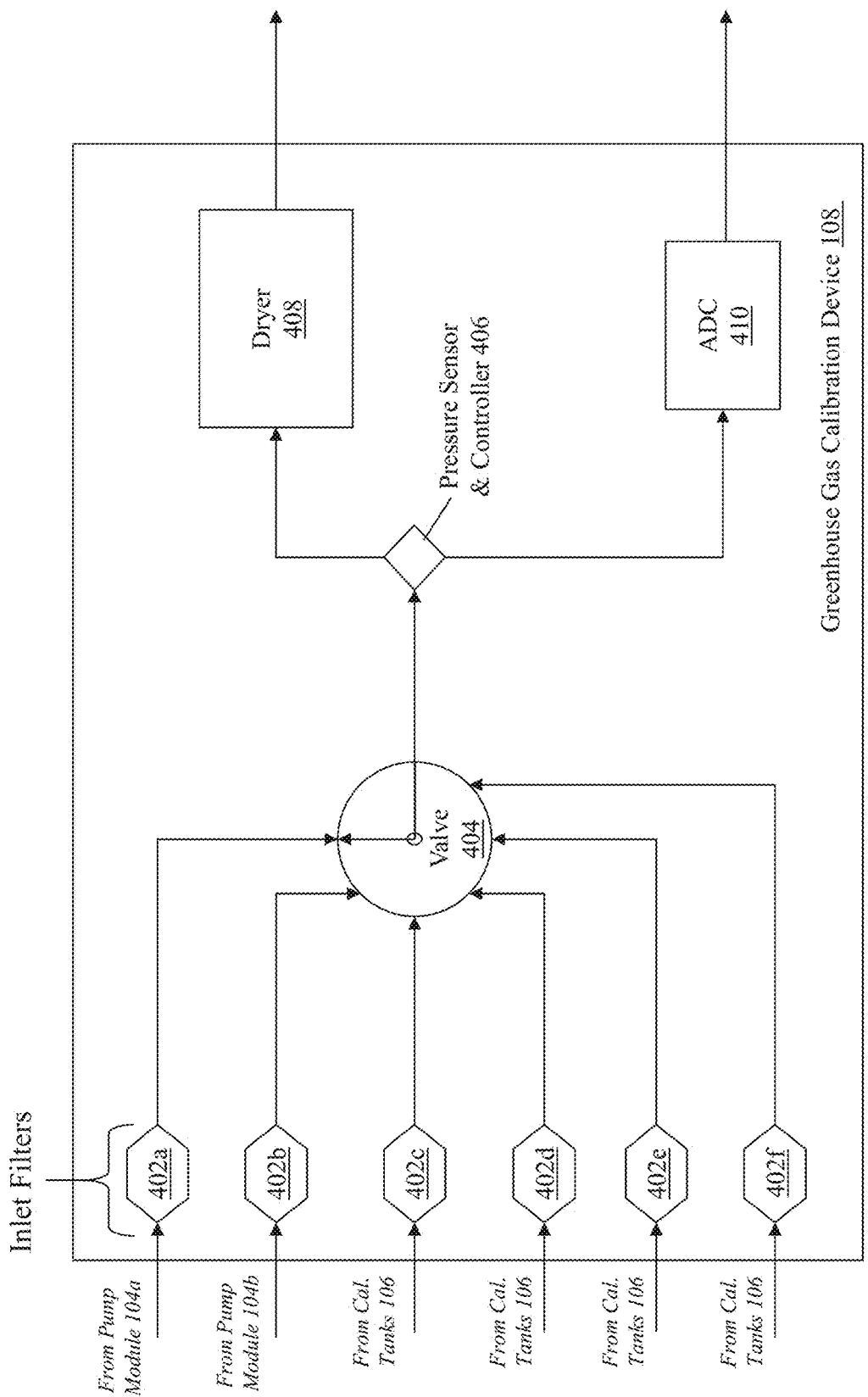
FIG. 4 is a detailed block diagram of the calibration device of the system for measuring greenhouse gas in the atmosphere.

As shown in FIG. 1, the system 100 also includes a greenhouse gas calibration device 108. FIG. 4 is a detailed block diagram 400 of the calibration device 108 used by the system 100. The low-flow pump module 113 (shown in FIG. 1) operates to draw the sampled gas from the high-flow pump modules 104a and 104b through the greenhouse gas calibration device 108 and the greenhouse gas measurement device 110. The calibration device 108 also receives calibration gas from the plurality of calibration tanks 106. The calibration device 108 includes an inlet and corresponding inlet filter (e.g., 402a-402f) for each of the sources of gas received by the device 108. The inlet filters 402a-402f remove unwanted substances from the received gases. It should be appreciated that the calibration device 108 can include any number of inlets and inlet filters. In some embodiments, the calibration device 108 includes a spare inlet filter (not shown) that is not used by the system 100 during normal operation. The spare inlet filter can be used to connect an external gas source (e.g., tank) for purposes of maintaining or testing the calibration device 108. For example, a technician can connect a tank to the calibration device 108 to perform manual processes or analysis when servicing the device.

The calibration device 108 also includes a valve 404 that is coupled to each of the inlets and inlet filters 402a-402f. The valve 404 has an individual port for each of the corresponding inlet filters 402a-402f. The valve 404 is also coupled to a pressure sensor and controller 406. The valve 404 is configured to sample gas, either coming from the pumps having sampled air or from the calibration tanks, from at least one of the inlet filters 402a-402f and transmit the gas to the pressure sensor and controller 406. The valve 404 can be configured to step incrementally through continuous revolutions, using microelectric and/or universal actuators. The valve 404 can select and isolate a stream of gas received from one of the inlet filters 402a-402f and transmit the selected stream to the pressure sensor 406. The valve 404 can dead-end or trap the gases from the remaining inlet filters 402a-402f when they are not selected.

In some embodiments, the valve 404 is coupled to a control mechanism (e.g., a microprocessor) (not shown) that determines which inlet filter(s) 402a-402f to open for sampling purposes. In some embodiments, the valve 404 is a Valco selector valve, available from Valco Instruments Co., Inc. The valve 404 is coupled to each of the inlet filters 402a-402f and the pressure sensor and controller 406 via conduits (e.g., 1/16-inch stainless steel tubing).

The calibration device 108 also includes a pressure sensor and controller 406 (PSC) that receives a flow of gas from the valve 404. The PSC 406 is coupled to a gas dryer 408, and regulates the pressure level of the gas flow before the gas is transmitted to the dryer 408. The PSC 406 also measures the pressure of the received gas flow. The PSC 406 is coupled to an analog-to-digital converter (ADC) 410 and transmits the measured pressure value to the ADC 410. In some embodiments, the PSC 406 is further configured to measure the temperature of the received gas flow and transmit the temperature to the ADC 410.

The gas dryer 408 operates to apply a drying agent to the gas received from the PSC 406 to prepare the gas for the measurement device 110. In some embodiments, the gas dryer 408 uses Nafion® tubing to reduce moisture content of the gas sample without affecting the amount of greenhouse gas present in the sample that is to be measured by the measurement device 110. Drying of the sampled atmospheric gas increases the accuracy and reliability of the greenhouse gas measurements provided by the measurement device 110.

The calibration device 108 also includes an ADC 410. The ADC 410 receives signals from the PSC 406 that represent pressure readings of the sampled gas. The ADC converts the signals into a digital form, and transmits the digital signals to a communications network (e.g., network 114 of FIG. 1). In some embodiments, the ADC 410 is coupled to the measurement device 110 via the network 114. This allows the measurement device 110 to record the pressure readings in conjunction with the device's analysis of the atmospheric gas sample.

Returning to FIG. 1, the system 100 also includes a greenhouse gas measurement device 110. The measurement device 110 receives sampled gas from the calibration device 108 and measures the amount of greenhouse gas present in the sample. In some embodiments, the measurement device 110 uses a cavity ring-down laser spectroscopy technique to determine the concentration of greenhouse gas. It should be appreciated that other measuring techniques can be used to determine the concentration of greenhouse gas without departing from the spirit or scope of the invention.

The measurement device 110 includes an internal computer (e.g., processor, computing device) that executes software to manage the measuring instrument (e.g., laser sensor) measuring the gas, and to capture and process the measurements and related information. The internal computer includes standard networking capabilities (e.g., Ethernet, PSTN modem) to allow the measurement device 110 to communicate with remote computing services (e.g., a central server) and other measurement devices distributed in a geographical area. The measurement device 110 can use the network connection to receive data from and transmit data to external sources (e.g., cloud-based storage, centralized database). In some embodiments, the measurement device 110 can use scheduling information from a local computing device. In some embodiments, the measurement device 110 can receive scheduling information from a central server computing device. Based on the scheduling information, the measurement device 110 can perform measurements at specific dates/times or in response to a specific scheduling instruction. In some embodiments, the scheduling information is transmitted from a central server computing device 110 in real time.

In some embodiments, the scheduling information includes calibration schedules which instruct the measurement device 110 to conduct a calibration routine. The calibration schedules can be chosen at random time intervals, or with break periods of, e.g., forty-eight hours. The scheduling information can also include a sampling schedule comprising a rolling time period during which samples of atmospheric gas are regularly taken from the external ports 102a and 102b. The scheduling information can also include subroutines for use with the calibration and sampling schedules (e.g., external port selection, valve adjustment, duration of sampling, pressure settings).

In another example, where multiple measurement devices comprise a distributed greenhouse gas monitoring network, the measurement device 110 can share its measurement results with other measurement devices to perform intra-calibration between devices. In another example, the measurement device 110 can transmit diagnostic information (e.g., error alerts, status checks) to a central server computing device so that appropriate maintenance can be provided. In some embodiments, maintenance can be provided remotely without the need for manually visiting the site where the system 100 is located. The measurement device 110 is also coupled to a local computing device (not shown) and display device 112 (e.g., monitor) that presents the measurement results to a user. In some embodiments, the measurement information is shared between the measurement devices in real time.

Figure 5:
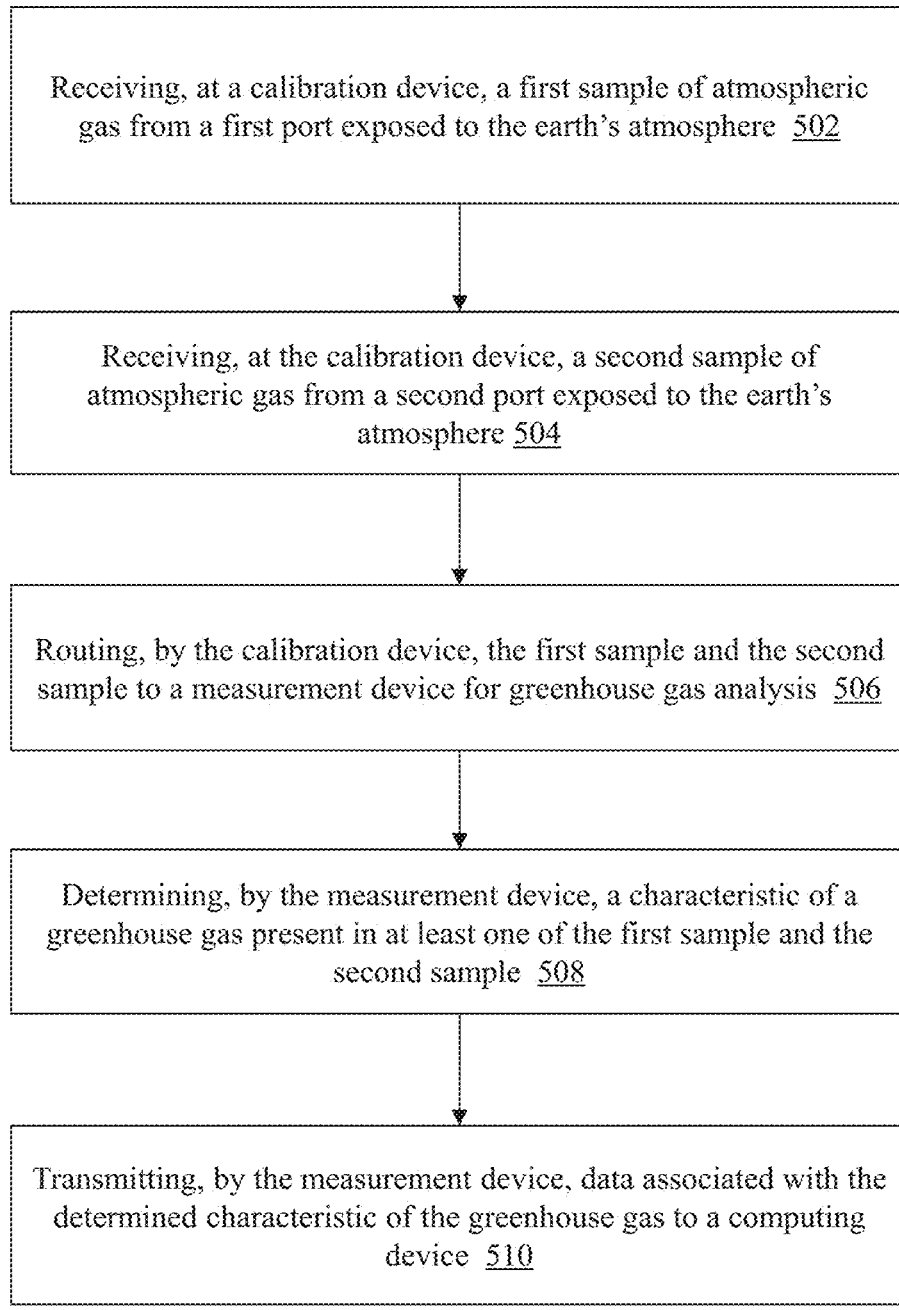
FIG. 5 is a flow diagram of a method for measuring greenhouse gas in the atmosphere.

FIG. 5 is a flow diagram of a method 500 for measuring greenhouse gas in the atmosphere using the system 100. The calibration device 108 receives (502) a first sample of atmospheric gas from a first port 102a exposed to the earth's atmosphere. The calibration device 108 receives (504) a second sample of atmospheric gas from a second port 104b exposed to the earth's atmosphere. The calibration device 108 routes (506) the first sample and the second sample to a measurement device 110 for greenhouse gas analysis. The measurement device 110 determines (508) a characteristic of a greenhouse gas present in at least one of the first sample and the second sample. The measurement device 110 transmits (510) data associated with the determined characteristic of the greenhouse gas to a computing device (e.g., an internal computer or an external computer). The system 100 can be configured to measure any number of gases present in the earth's atmosphere, including but not limited to carbon dioxide ($CO_2$), methane ($CH_4$), and carbon monoxide (CO).

In some embodiments, upon performing a measurement of the atmospheric gas, the measurement device 110 generates a data packet with a number of different characteristics and/or parameters. Some of the characteristics include, but are not limited to, concentration of greenhouse gas in the sample (wet vs. dry), concentration of water vapor ($H_2O$) in the sample, position of the valve 404 in the calibration device 108 (e.g., the port from which the sample was taken), temperature (e.g., ° C.) inside the calibration device 108, pressure inside the cavity used for laser spectroscopy, temperature inside the cavity, current of the laser, and timestamp of a measurement. These characteristics can be recorded by the internal computer of the measurement device 110 and used for quality control purposes and to ensure that the measurement device 110 is operating properly.

Figure 6:
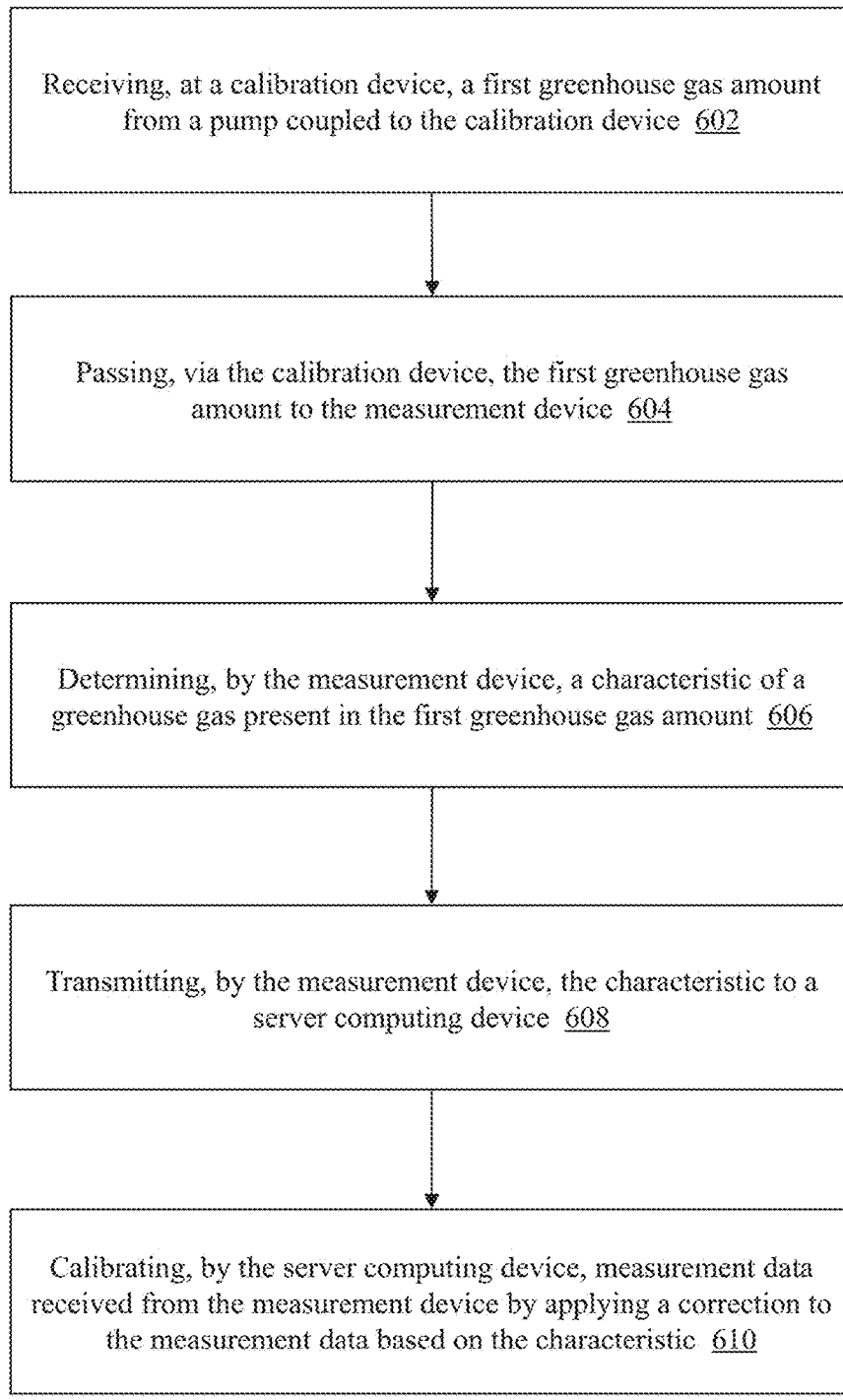
FIG. 6 is a flow diagram of a method for calibrating a greenhouse gas measurement device.

FIG. 6 is a flow diagram of a method 600 for calibrating a greenhouse gas measurement device (e.g., measurement device 110 of FIG. 1). A calibration device (e.g., calibration device 108) receives (602) a first greenhouse gas amount from a pump (e.g., pump 208 in FIG. 2) coupled to the calibration device 108. For example, the calibration device 108 can be configured to sample gas from one of the calibration tanks 302, 304, 306, 308 via the valve 404. The calibration device 108 passes (604) the first sampled gas amount to the measurement device 110 (e.g., via the PSC 406 and dryer 408). The measurement device 110 determines (606) a characteristic of a greenhouse gas present in the first greenhouse gas amount. In some embodiments, the characteristic includes a concentration of the greenhouse gas, an identifying property of the greenhouse gas, or other types of characteristics. The measurement device 110 transmits (608) the characteristic to a server computing device (e.g., via the network 114). The server computing device calibrates (610) greenhouse gas measurement data received from the measurement device 110 by applying a correction to the measurement data based on the characteristic.

Figure 7:
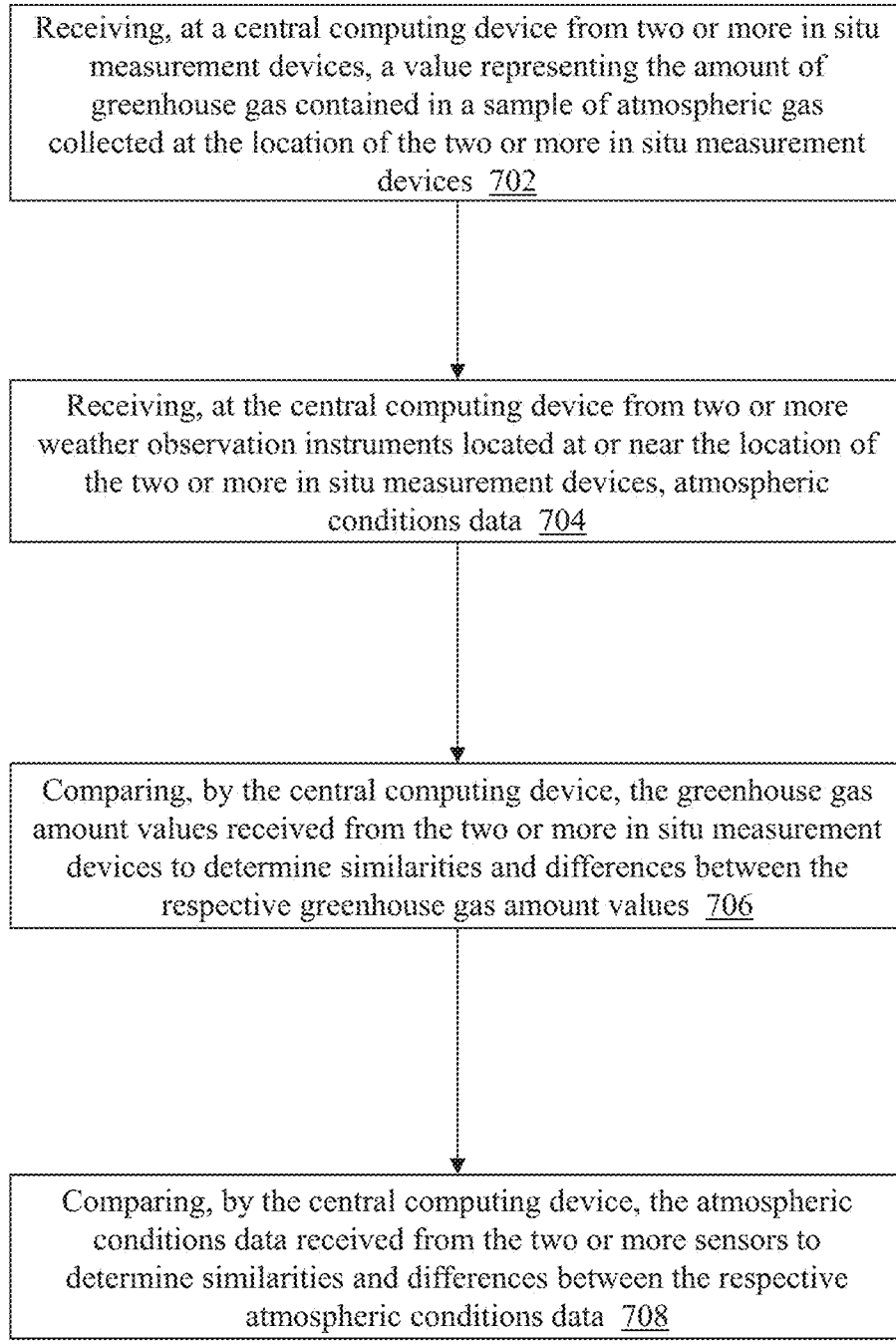
FIG. 7 is a flow diagram of a method for measuring greenhouse gas using a network of geographically distributed nodes.
Figure 8:
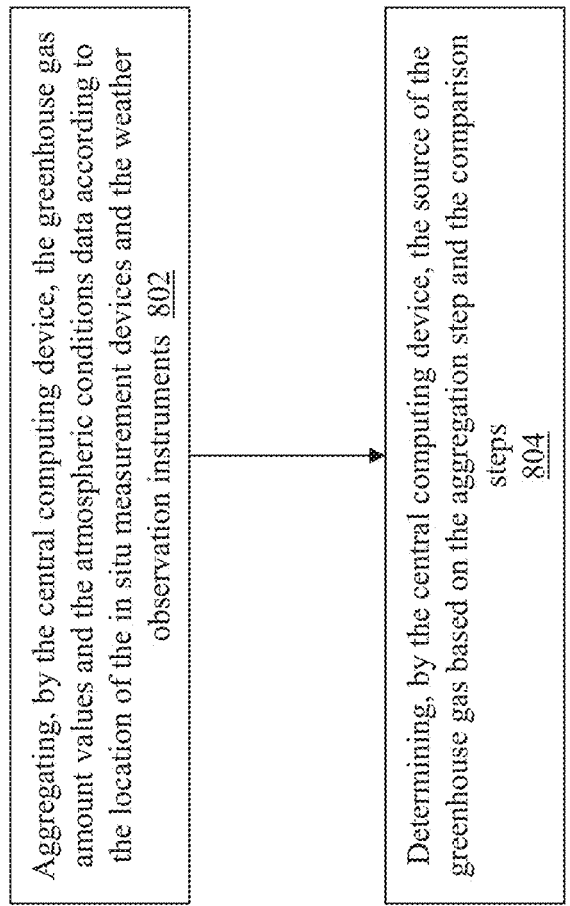
FIG. 8 is a flow diagram of a method for determining a source of greenhouse gas using data obtained by a network of geographically distributed nodes.
Figure 9:
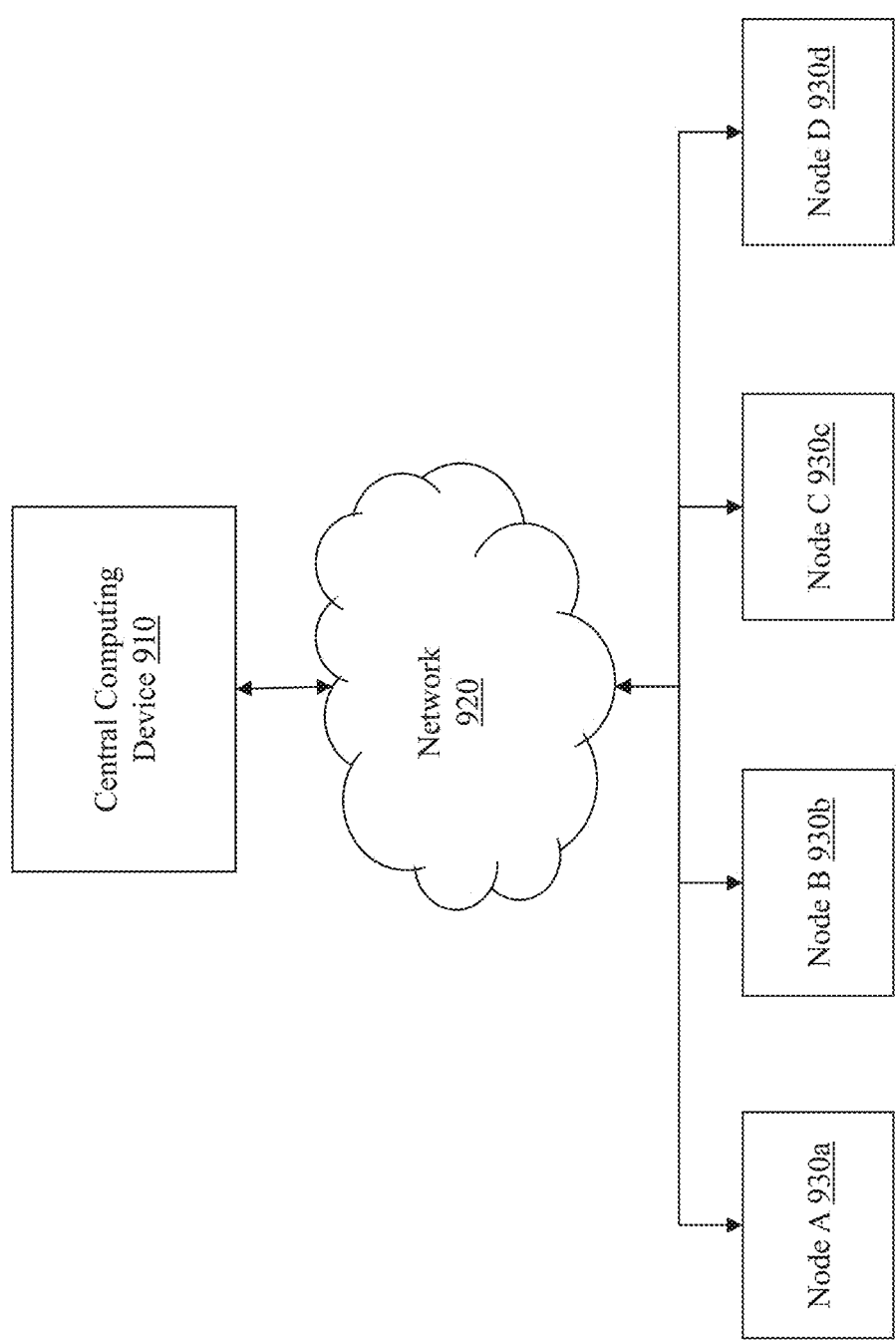
FIG. 9 is a block diagram of a network of geographically distributed nodes for measuring greenhouse gas in the atmosphere.

Once the system 100 has conducted greenhouse gas measurements of atmospheric gas and recorded the associated data, the system 100 transmits the data to a server computing device via the communication network 114 for further analysis and reporting to determine potential sources of the greenhouse gas. FIG. 7 is a flow diagram of a method 700 for measuring greenhouse gas using a network of geographically distributed nodes, where each node includes system 100. FIG. 8 is a flow diagram of a method 800 for determining a source of greenhouse gas using data obtained by the network of geographically distributed nodes. FIG. 9 is a block diagram of a network 900 of geographically distributed nodes using system 100. The network 900 includes a server computing device 910 configured to communicate via a communications network 920 with a plurality of nodes 930a-930d, where a system 100, including the components depicted in FIG. 1, is located at each node 930a-930d.

A server computing device 910 receives (702), from two or more in situ measurement devices (e.g., measurement device 110 at nodes 930a-930d), a value representing the amount of greenhouse gas contained in a sample of atmospheric gas collected at the location of the two or more in situ measurement devices. The server computing device 910 receives (704), from two or more weather observation instruments located at or near the location of the two or more in situ measurement devices, atmospheric conditions data. In some embodiments, as described previously, the weather observation instruments are weather conditions equipment (e.g., Weather Station from Earth Networks, Inc.) located on the tower that also contains the ports 102a and 102b in FIG. 1. The weather observation instruments collect information about the current weather conditions at the location of each node 930a-930d and transmit the information to the server computing device 910 in conjunction with the sampled atmospheric gas.

The server computing device 910 compares (706) the greenhouse gas amount values received from the two or more in situ measurement devices to determine similarities and differences between the respective greenhouse gas amount values. The server computing device 910 compares (708) the atmospheric conditions data received from the two or more weather observation instruments to determine similarities and differences between the respective atmospheric conditions data.

The central computing device 910 aggregates (802) the greenhouse gas amount values and the atmospheric conditions data according to the location of the in situ measurement devices and the weather observation instruments. The central computing device 910 (804) determines the source of the greenhouse gas based on the aggregation step and the comparison steps.

One technique used to determine the source of the greenhouse gas is inverse modeling, where the amount of greenhouse gas emitted and the amount of greenhouse gas absorbed are measured. As part of the inverse modeling analysis, the server computing device 910 can estimate the location of greenhouse gas sinks (e.g., areas or entities that absorb greenhouse gas) and greenhouse gas sources (e.g., areas or entities that emit greenhouse gas) over a geographical area. Once the server computing device 910 has collected the greenhouse gas readings and atmospheric conditions data from each of the distributed nodes 930a-930d, the server computing device 910 can determine from where the parcels of air sampled by each of the nodes are coming. The analysis can also include application of a probability function to the detected greenhouse gas amounts to account for changes in the atmospheric conditions, such as turbulence, mixing between layers of the atmosphere, wind shifts, and the like.

In some embodiments, inverse models at regional scales consider a three-dimensional domain surrounding an area of interest in the observing network. An observation measured at a tower in the 3D domain differs from an average background value, due to contributions from emissions or uptakes taking place on the surface within the area of interest, and from parcels of air carrying tracer gases through lateral and top boundaries of the domain. Negligible changes in mixing ratio of tracer gases can take place in the atmosphere due to chemical reactions, and can be omitted as relatively small. The flow within the domain and through the boundaries depends on atmospheric conditions, and the flow can be estimated either from weather observations, from a numerical model, or a combination of both. Inverse modeling determines the contribution due to emissions or uptakes of tracer gases within the area of interest and quantifies those geographically distributed emissions and uptakes with some uncertainties.

FIG. 10 is a diagram of a computed matrix of surface impacts 1000 based on the measurements of greenhouse gases by the network that is a step in the inversion report generated by the system 100 for measuring greenhouse gas in the atmosphere. The computed matrix 1000 includes a geographical grid 1010 with circles representing the location of nodes 930a-930d of the network 900 shown in FIG. 9, and the arrows represent the speed (e.g., a longer arrow means greater speed) and direction of the air flow in the atmosphere, as recorded by the weather observation instruments in the network 900. As shown in FIG. 10, the air flow is traveling in a southeasterly direction from the top left corner of the grid, and the speed decreases from north to south. The italicized numerals next to each node in FIG. 10 represent the concentration of greenhouse gas detected by the individual node, on a scale from 0-10 with 10 being highest. Although each sector of the grid 1010 depicted in FIG. 10 does not include a node, it should be appreciated that the server computing device 910 in some embodiments can estimate a concentration of greenhouse gas in those sectors based on the data received from the existing nodes. While the grid 1010 in FIG. 10 is represented in two dimensions, flow transporting parcels of air containing greenhouse gases can be presented in one, two, or three dimensions. Also, when presented in three dimensions, flow can be detached from the surface, where sources and sinks of greenhouse gases are located, and at those times mixing ratios of greenhouse gases within the flow are not impacted by sources and sinks, but transported horizontally and can be diffused vertically. In some embodiments, the computed impacts of surface sources and sinks on the measurements of greenhouse gases by the network are stored as matrices at a central server computing device.

Based on the computed matrix 1000 and measurements in the network, it can be determined that the contribution from sources of greenhouse gases is highest in the top left corner of the geographical grid 1010 and that the contributions from the remaining portions of the grid 1010 are smaller. In addition, the winds are recorded or simulated for all grid cells. In light of this information, the server computing device 910 (or alternatively, a user analyzing the computed matrix) can determine when the parcels that carry the greenhouse gas originating at a given grid cell travel from the geographic area of this grid cell to any of the greenhouse gas measuring devices in the network.

In some embodiments, the grid 1010 can be combined with pre-stored information about the geographic area, including the location of known greenhouse gas sources or sinks. For example, a factory known for emitting a large amount of greenhouse gas could be located just northwest of the top left corner of the grid. The server computing device 910 can augment the grid with this information and determine that the factory is a potential or likely source of the greenhouse gas detected by the nodes. Appropriate steps can be taken by, e.g., local or state agencies to regulate the emissions produced by the factory or levy penalties on the owner of the factory. In some embodiments, the location of greenhouse gas sinks and sources can be determined along with an uncertainty range.

In another example, the computed matrix 1000 shows that between the middle and bottom of the left portion of the grid 1010, the contribution of greenhouse gases from sources and uptakes drops significantly (e.g., from seven to two), and when parcels originating from this area are mixed with parcels previously enriched with greenhouse gases while over the left top corner, the resulting greenhouse gas measurement at location two changes only moderately. Further analysis can be conducted with respect to the geographical area between those two nodes to determine magnitudes of potential greenhouse gas sources or sinks located there depending on increases or decreases in greenhouse gas measurements within the network. The determined magnitudes of sources and sinks in the area and the uncertainties associated with computation are provided as an inversion report.

The above-described techniques can be implemented in digital and/or analog electronic circuitry, or in computer hardware, firmware, software, or in combinations of them. The implementation can be as a computer program product, i.e., a computer program tangibly embodied in a machine-readable storage device, for execution by, or to control the operation of, a data processing apparatus, e.g., a programmable processor, a computer, and/or multiple computers. A computer program can be written in any form of computer or programming language, including source code, compiled code, interpreted code and/or machine code, and the computer program can be deployed in any form, including as a stand-alone program or as a subroutine, element, or other unit suitable for use in a computing environment. A computer program can be deployed to be executed on one computer or on multiple computers at one or more sites.

Method steps can be performed by one or more processors executing a computer program to perform functions of the invention by operating on input data and/or generating output data. Method steps can also be performed by, and an apparatus can be implemented as, special purpose logic circuitry, e.g., a FPGA (field programmable gate array), a FPAA (field-programmable analog array), a CPLD (complex programmable logic device), a PSoC (Programmable System-on-Chip), ASIP (application-specific instruction-set processor), or an ASIC (application-specific integrated circuit), or the like. Subroutines can refer to portions of the stored computer program and/or the processor, and/or the special circuitry that implement one or more functions.

Processors suitable for the execution of a computer program include, by way of example, both general and special purpose microprocessors, and any one or more processors of any kind of digital or analog computer. Generally, a processor receives instructions and data from a read-only memory or a random access memory or both. The essential elements of a computer are a processor for executing instructions and one or more memory devices for storing instructions and/or data. Memory devices, such as a cache, can be used to temporarily store data. Memory devices can also be used for long-term data storage. Generally, a computer also includes, or is operatively coupled to receive data from or transfer data to, or both, one or more mass storage devices for storing data, e.g., magnetic, magneto-optical disks, or optical disks. A computer can also be operatively coupled to a communications network in order to receive instructions and/or data from the network and/or to transfer instructions and/or data to the network. Computer-readable storage mediums suitable for embodying computer program instructions and data include all forms of volatile and non-volatile memory, including by way of example semiconductor memory devices, e.g., DRAM, SRAM, EPROM, EEPROM, and flash memory devices; magnetic disks, e.g., internal hard disks or removable disks; magneto-optical disks; and optical disks, e.g., CD, DVD, HD-DVD, and Blu-ray disks. The processor and the memory can be supplemented by and/or incorporated in special purpose logic circuitry.

To provide for interaction with a user, the above described techniques can be implemented on a computer in communication with a display device, e.g., a CRT (cathode ray tube), plasma, or LCD (liquid crystal display) monitor, for displaying information to the user and a keyboard and a pointing device, e.g., a mouse, a trackball, a touchpad, or a motion sensor, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributed computing system that includes a front-end component. The front-end component can, for example, be a client computer having a graphical user interface, a Web browser through which a user can interact with an example implementation, and/or other graphical user interfaces for a transmitting device. The above described techniques can be implemented in a distributed computing system that includes any combination of such back-end, middleware, or front-end components.

The components of the computing system can be interconnected by transmission medium, which can include any form or medium of digital or analog data communication (e.g., a communication network). Transmission medium can include one or more packet-based networks and/or one or more circuit-based networks in any configuration. Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), Bluetooth, Wi-Fi, WiMAX, general packet radio service (GPRS) network, HiperLAN), and/or other packet-based networks. Circuit-based networks can include, for example, the public switched telephone network (PSTN), a legacy private branch exchange (PBX), a wireless network (e.g., RAN, code-division multiple access (CDMA) network, time division multiple access (TDMA) network, global system for mobile communications (GSM) network), and/or other circuit-based networks.

Information transfer over transmission medium can be based on one or more communication protocols. Communication protocols can include, for example, Ethernet protocol, Internet Protocol (IP), Voice over IP (VOIP), a Peer-to-Peer (P2P) protocol, Hypertext Transfer Protocol (HTTP), Session Initiation Protocol (SIP), H.323, Media Gateway Control Protocol (MGCP), Signaling System #7 (SS7), a Global System for Mobile Communications (GSM) protocol, a Push-to-Talk (PTT) protocol, a PTT over Cellular (POC) protocol, and/or other communication protocols.

Devices of the computing system can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a World Wide Web browser (e.g., Microsoft® Internet Explorer® available from Microsoft Corporation, Mozilla® Firefox available from Mozilla Corporation). Mobile computing device include, for example, a Blackberry®. IP phones include, for example, a Cisco® Unified IP Phone 7985G available from Cisco Systems, Inc, and/or a Cisco® Unified Wireless Phone 7920 available from Cisco Systems, Inc.

Comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein.

What is claimed is:

1. A device for calibrating a greenhouse gas measurement device, the device comprising:
a plurality of inlets for receiving samples of atmospheric gas from a plurality of ports exposed to the earth's atmosphere, wherein each of the one or more ports is positioned at a different level of the atmosphere; one or more pumps for regulating a flow of the atmospheric gas received via the inlets; one or more calibration tanks; a sampling module comprising:
a valve coupled to the one or more pumps and the one or more calibration tanks, a pressure and temperature controller, and a dryer;
the sampling module configured to:
sample gas of each of the plurality of ports from one or more of the pumps using the valve;
regulate pressure and temperature of the sampled gas of each of the plurality of ports using the pressure and temperature controller; remove water vapor from the sampled gas of each of the plurality of ports using the dryer; and
convey the sampled gas of each of the plurality of ports from the dryer to a measurement device;
sample gas from at least one of the one or more calibration tanks using the valve;
convey the sampled gas of at least one of the one or more calibration tanks to the measurement device; the measurement device comprising: a processor; a memory module; and
an internal measurement sensor; the measurement device configured to:
determine a characteristic of a greenhouse gas present in the sampled gas of the at least one of the one or more calibration tanks using the internal measurement sensor;
compare the determined characteristic of the greenhouse gas present in the sampled gas of the at least one of the one or more calibration tanks to an expected value for the determined characteristic;
adjust the measurement device for subsequent greenhouse gas analysis when the determined characteristic of the greenhouse gas present in the sampled gas of the at least one of the one or more calibration tanks is different than the expected value for the determined characteristic;
determine a characteristic of a greenhouse gas present in a first sample of gas from one of the plurality of ports at a first level of the atmosphere using the internal measurement sensor;

determine a characteristic of a greenhouse gas present in a second sample of gas from another of the plurality of ports at a second level of the atmosphere using the internal measurement sensor;

record, at the memory module, parameters of the measurement device during the steps of determining the characteristic of the greenhouse gas present in the first sample of gas and determining the characteristic of the greenhouse gas present in the second sample of gas; and adjust the measurement device for subsequent greenhouse gas analysis based upon the recorded parameters.

2. The device of claim 1, wherein the sampling module is further configured to:

measure the pressure of the sampled gas of the at least one of the one or more calibration tanks; and transmit the measured pressure value to the measurement device.

3. The device of claim 1, further comprising a sampling controller coupled to the valve configured to instruct the valve to sample gas from one of the one or more pumps or one of the one or more calibration tanks.

4. The device of claim 3, wherein the sampling controller instructs the valve to sample gas from the one or more pumps and the one or more calibration tanks in a predetermined sequence.

5. The device of claim 1, wherein the inlets are coupled to the ports via a tube.

6. The device of claim 1, wherein the atmospheric gas received by j least one of the plurality inlets is air.

7. The device of claim 1, wherein at least one of the one or more calibration tanks contains a gas used for zeroing the calibration device.

8. The device of claim 1, wherein the valve is further coupled to an auxiliary intake configured to access an additional gas source.

9. The device of claim 1, wherein the sampling device is further configured to:

receive quality control data from the calibration device; and adjust the sampling of gas based on the quality control data.

* * * * *